US00PP19054P3

(12) United States Plant Patent

Leis et al.

(10) Patent No.: US PP19,054 P3

(45) Date of Patent: Jul. 29, 2008

(54) APPLE TREE NAMED 'FUJIKO'

(50) Latin Name: *Malus domestica*
Varietal Denomination: Fujiko

(75) Inventors: Michelangelo Leis, Ferrara (IT); Carlo Mazzola, Ferrara (IT)

(73) Assignee: Consorzio Italiano Vivaisti, S. Giuseppe de Comacchio (FE) (IT)

( * ) Notice: Subject to any disclaimer, the term of this patent is extended or adjusted under 35 U.S.C. 154(b) by 0 days.

(21) Appl. No.: 11/727,223

(22) Filed: Mar. 26, 2007

(65) Prior Publication Data

US 2007/0226855 P1 Sep. 27, 2007

(30) Foreign Application Priority Data

Mar. 27, 2006 (QZ) ..... 2006/0766

(51) Int. Cl.
*A01H 5/00* (2006.01)

(52) U.S. Cl. ..... Plt./168

(58) Field of Classification Search ..... Plt./168
See application file for complete search history.

*Primary Examiner*—Annette H Para
(74) *Attorney, Agent, or Firm*—Foley & Lardner LLP

(57) ABSTRACT

A new and distinct *Malus domestica* apple tree variety named 'FUJIKO' particularly characterized by having intense red color on most of the skin surface; red coloration on the unexposed side of the fruit; and good overcolor of the fruits underexposed to the sun light.

6 Drawing Sheets

PRIORITY CLAIM

This application claims priority under 35 U.S.C. § 119(f) of the European Union — Community Plant Variety Rights No. 2006/0766 filed Mar. 27, 2006.

Latin name of the genus and species of the plant claimed: *Malus domestica.*

Variety denomination: 'FUJIKO'.

BACKGROUND OF THE INVENTION

The present invention relates to a new and distinct variety of apple tree, botanically known as *Malus domestica Mill.* of the family Rosaceae, and hereinafter referred to by the variety denomination 'FUJIKO'.

The new *Malus* 'FUJIKO' was discovered by the inventors, Michelangelo Leis and Carlo Mazzola, in the summer of 2002 in a block of Fuji apple tree designated as 'NAGAFU 12' (unpatented), growing in a cultivated area of an orchard in Migliaro, Ferrara, Italy. These trees of the new variety 'FUJIKO' were selected based on the distinctly different appearance of the fruits of 'FUJIKO' (more intense and diffused red skin surface color) from the fruit of the adjacent Fuji 'NAGAFU 12' trees.

The new *Malus* 'FUJIKO' was first selected from propagation and further testing by the inventors in 2002 in a controlled environment in Comacchio, Ferrara, Italy. Asexual reproduction of the new *Malus* 'FUJIKO' trees started by grafting onto M9 rootstock unpatented in February 2003 in a testing orchard near Comacchio, Ferrara, Italy. Some trees of Fuji 'NAGAFU 12' (unpatented), Fuji 'Raku Raku', Fuji, 'NAGAFU 6' (unpatented) and Fuji 'T.A.C. #114' (patented, U.S. Plant Pat. No. 8,032) were grafted on M9 roostocks in the same row and at the same time as 'FUJIKO' was first grafted on M9 rootstocks. First fruiting of the 'FUJIKO' trees occurred in 2004, and revealed that first produced from the 'FUJIKO' trees possessed characteristics which clearly distinguished 'FUJIKO' from other known Fuji varieties.

Asexual reproduction of 'FUJIKO' has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'FUJIKO' which in combination distinguish this apple tree as a new and distinct variety from the other Fuji strains:

1. Intense red color on most of the skin surface;
2. Red coloration on the unexposed side of the fruit; and
3. Good overcolor of the fruits underexposed to the sun light.

In comparison to Fuji 'NAGAFU 12', 'FUJIKO' produces fruit with a more intense and diffused red skin surface color than fruit produced by 'NAGAFU 12'. Of the commercial cultivars known to the inventors, the most similar in comparison to 'FUJIKO' is the variety 'NAGAFU 12' as compared above.

BRIEF DESCRIPTION OF THE DRAWINGS

The accompanying photographs illustrate the overall appearance of the new apple tree 'FUJIKO' showing the colors as true as is reasonably possible with color reproductions of this type. Color in the photographs may differ slightly from the color value cited in the detailed botanical description, which accurately describe the color of 'FUJIKO'.

DETAILED BOTANICAL DESCRIPTION

Figure 1:
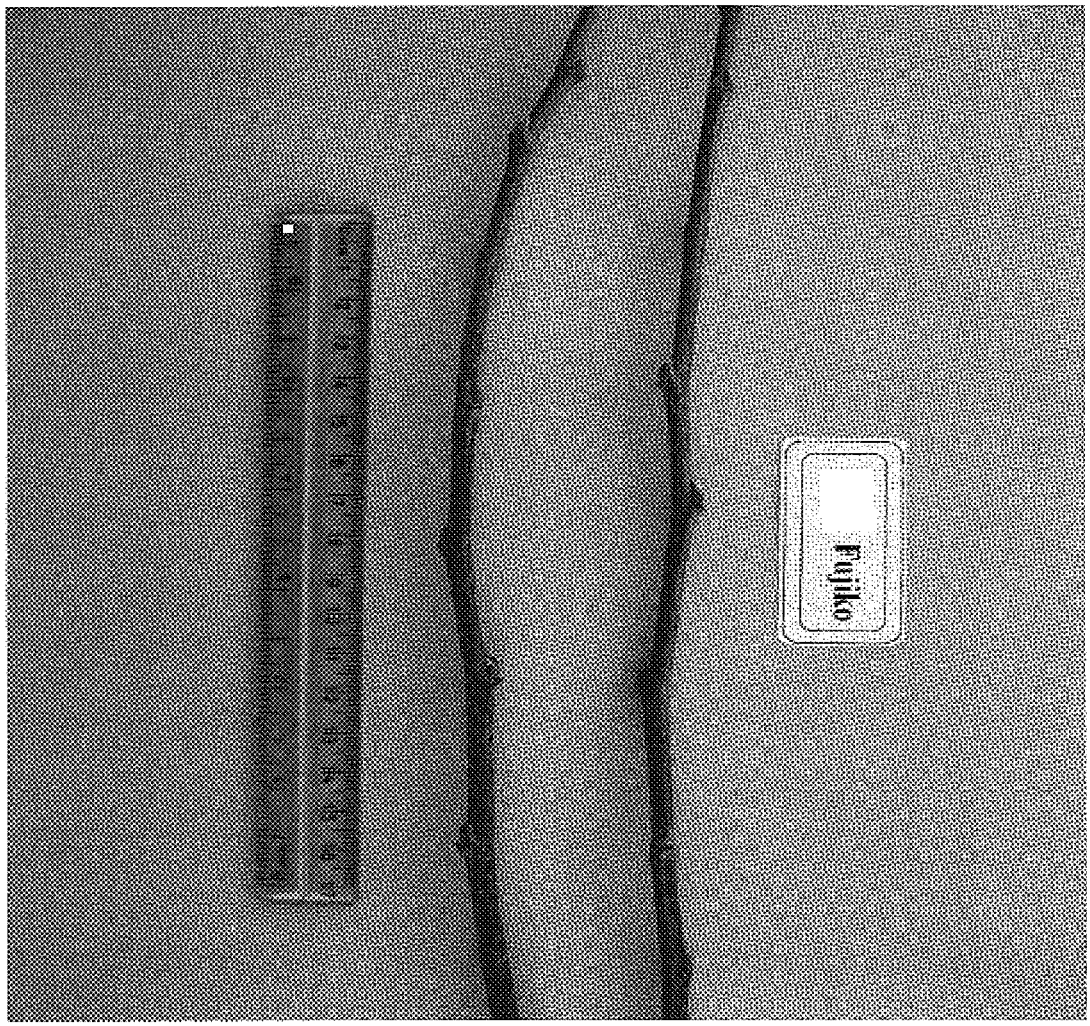
FIG. 1 shows dormant wood of 'FUJIKO'.
Figure 2:
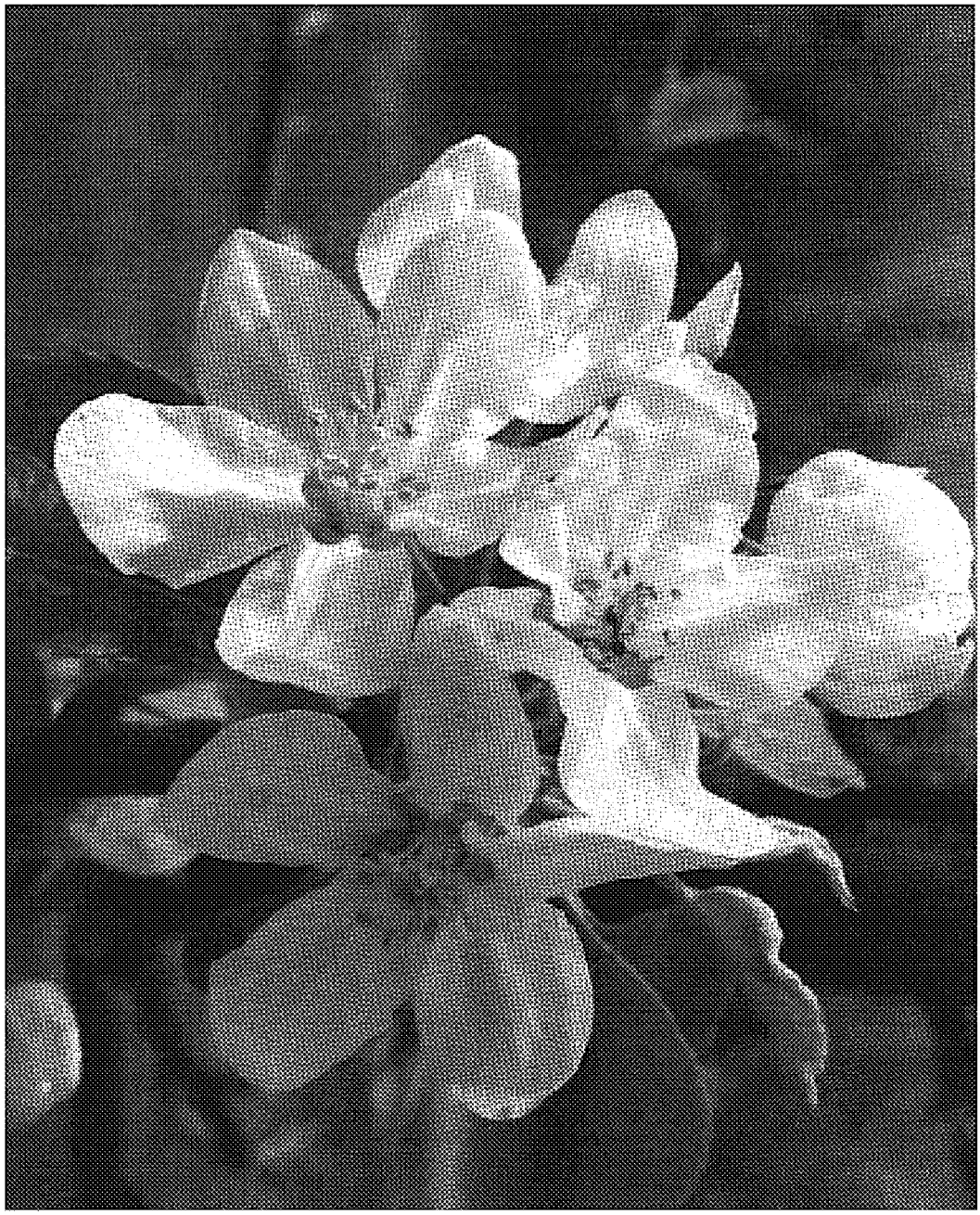
FIG. 2 shows typical inflorescence of 'FUJIKO'.
Figure 3:
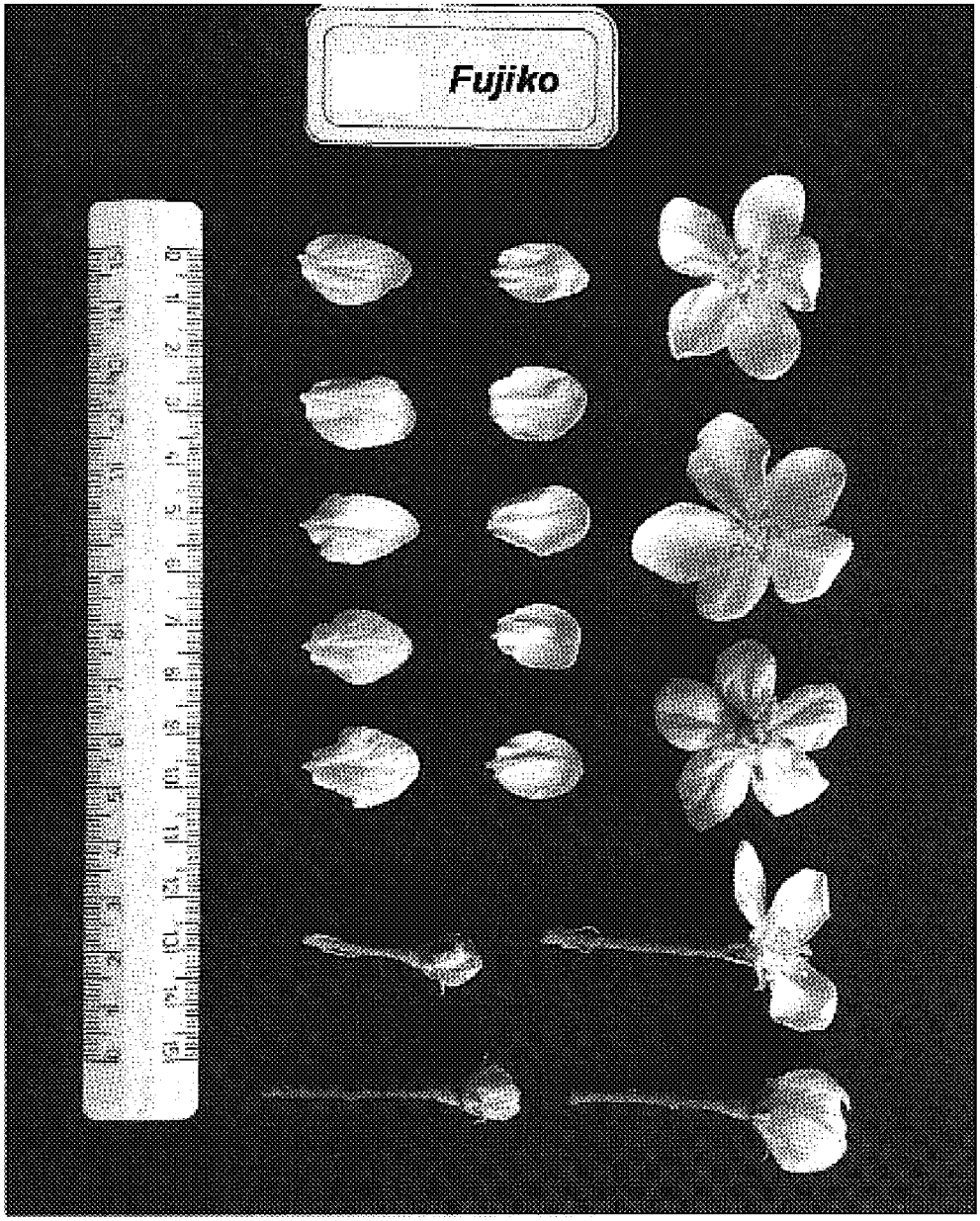
FIG. 3 shows a close-up of the different details of the inflorescence of 'FUJIKO'.
Figure 4:
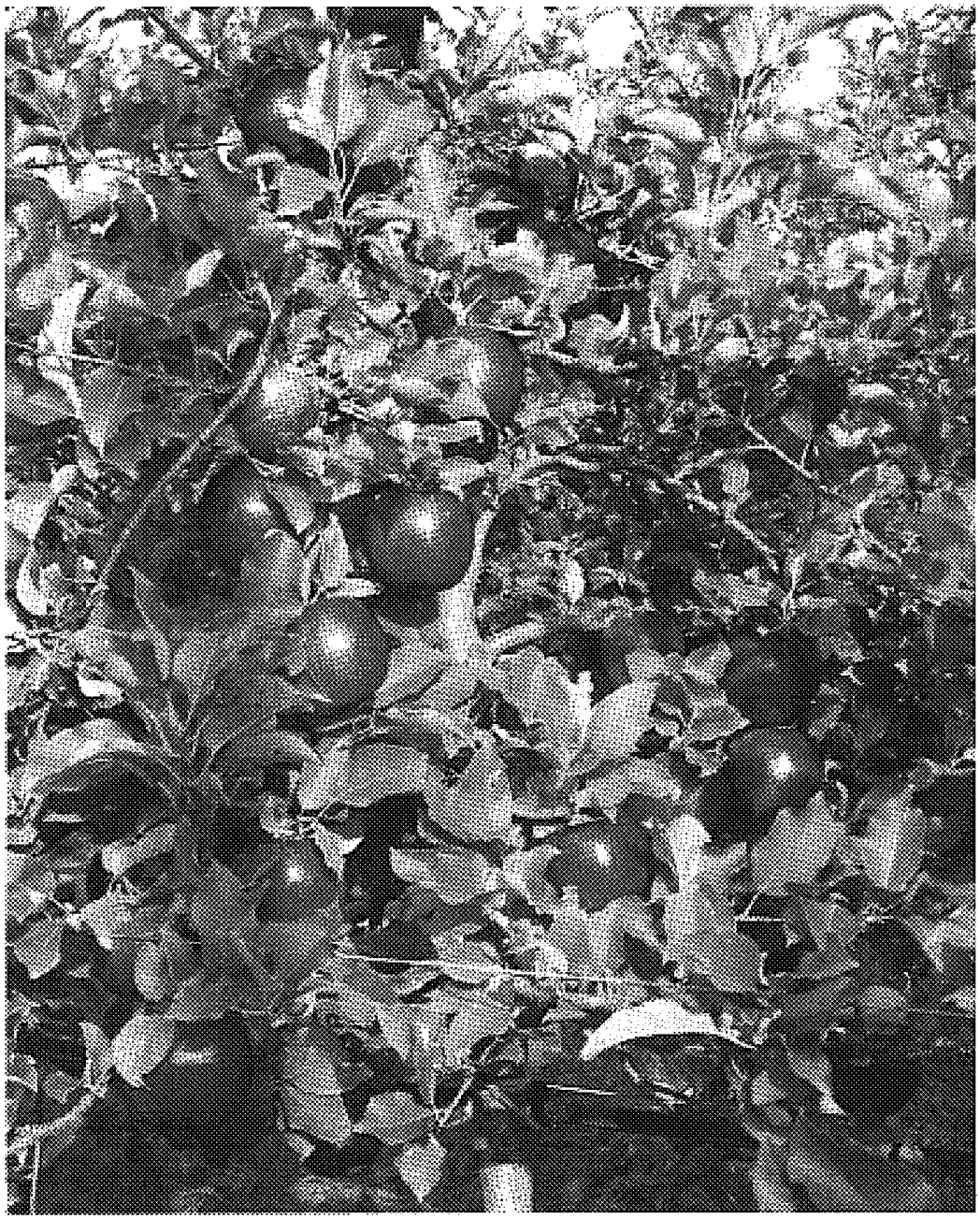
FIG. 4 shows a bearing tree of 'FUJIKO' in the second growth season in October of 2006.
Figure 5:
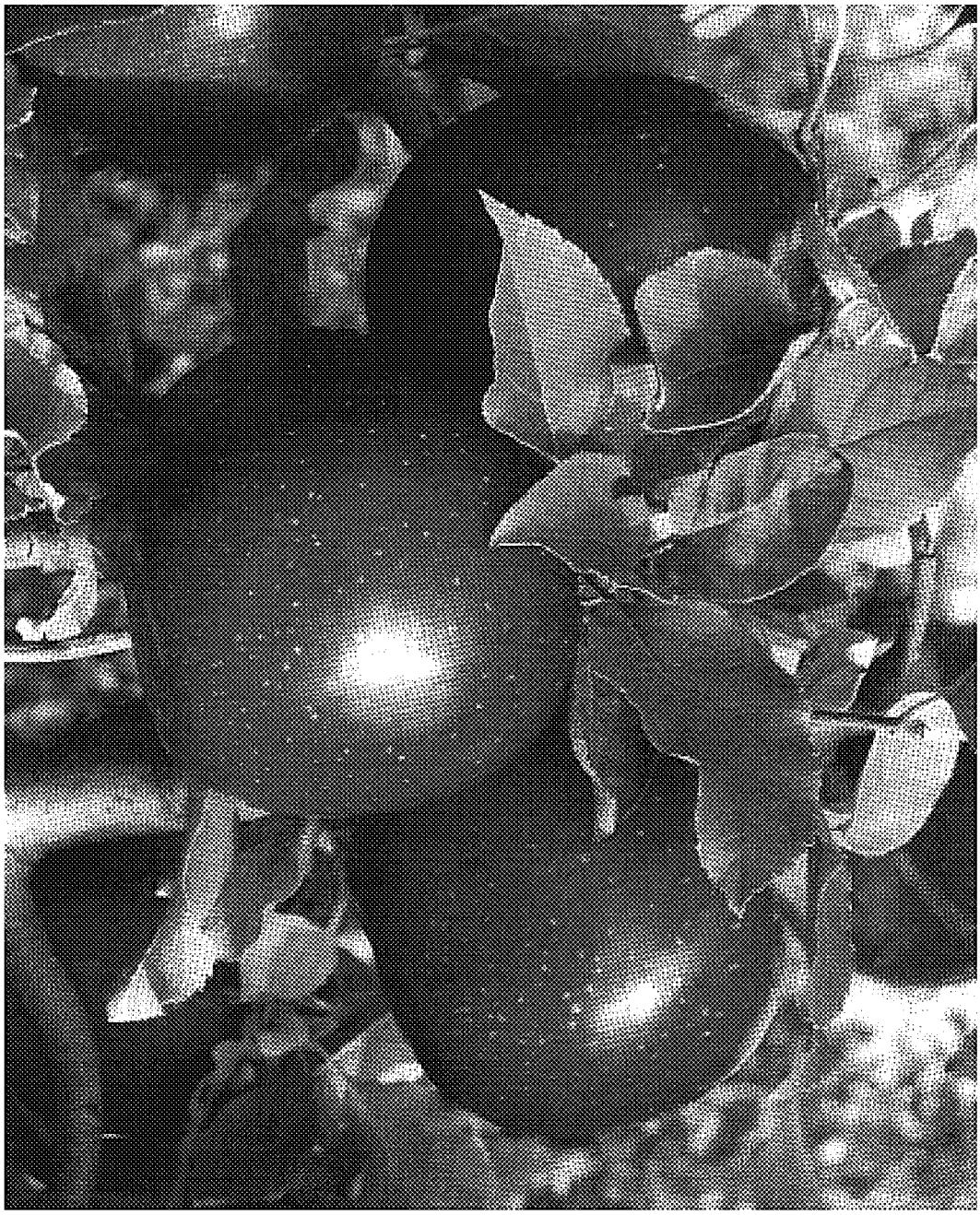
FIG. 5 shows a close-up of the typical mature fruit and leaves of 'FUJIKO'.
Figure 6:
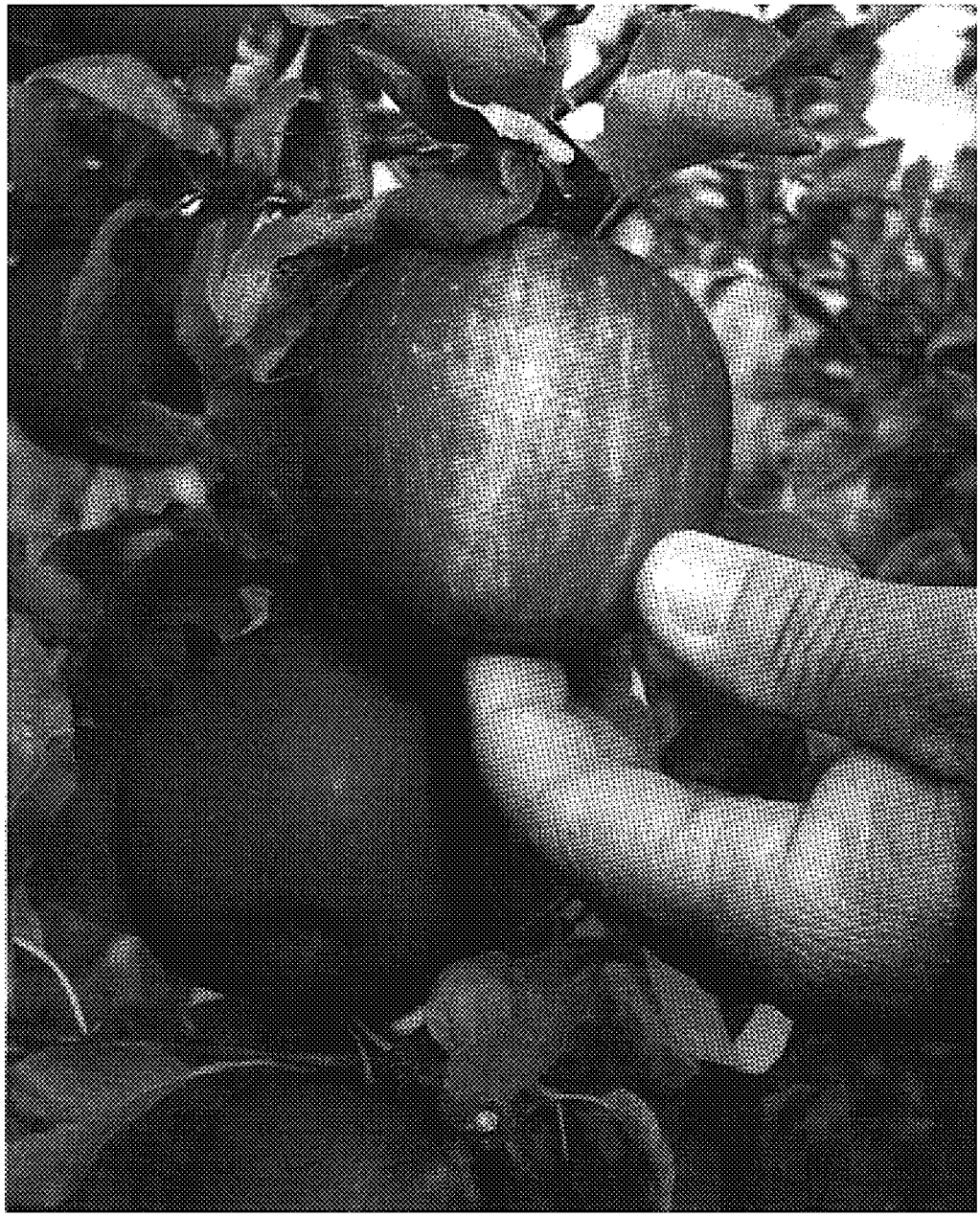
FIG. 6 shows the coloration of the typical mature fruits of 'FUJIKO' on the shaded side.

'FUJIKO' has not been observed under all possible environmental conditions The phenotype of the new variety may vary with variations in environment such as temperature, light intensity, and day length without any change in the genotype of the plant.

The aforementioned photographs, together with the following observations, measurements and values describe trees of 'FUJIKO' as grown in the apple farm in S. Giuseppe di Comacchio, Ferrara, Italy, under conditions which closely approximate those generally used in commercial practice. The apple farm where 'FUJIKO' is grown is situated near the Adriatic sea (44°45' North, 12°11' East) and is zero (0) meters above sea level. The soil of the apple farm where 'FUJIKO' is grown is sandy, and the soil is treated with manure every year and irrigated with drip irrigation systems. The climate is temperate continental with high summer temperatures and low winter temperatures.

Unless otherwise stated, the detailed botanical description includes observations, measurements and values based on four (4) year old 'FUJIKO' trees that were grown in the apple farm in S. Giuseppe di Comacchio, Ferrara, Italy, from 2005 to 2006. All trees were of cropping maturity. Quantified measurements are expressed as an average of measurements taken from a number of individual trees of 'FUJIKO'. The measurements of any individual tree, or any group of trees, of the new variety may vary from the stated average.

Color references are made to the Munsell Book of Color (MBC), except where general colors of ordinary significance are used. Color values were taken under daylight conditions at approximately at 10:00 am in S. Giuseppe di Comacchio, Ferrara, Italy.

All trees of 'FUJIKO', insofar as they have been observed, have been identical in all the characteristics described below.

Classification:
- *Botanical.*—*Malus domestica.*

Propagation:
- *Type.*—Budding and grafting on M9 rootstock.
- *Locality where grown and observed.*—S. Giuseppe di Comacchio, Ferrara, Italy.

Growing conditions:
- *Light intensities.*—Fully sunlight.
- *Temperature.*—During day, grown in range of 0° C. to 35° C., and during evening, grown in a range of −5° C. to 25° C. (based on the average month temperature).

Tree:
- *Age.*—Observed tree were four (4) years old.
- *Vigor.*—Vigorous, same as Fuji 'NAGAFU 12'.
- *Form.*—Somewhat spreading, branch angle is about 40° to 60° with respect to trunk if allowed to grow naturally.
- *Bearing.*—Annual to occasionally biennial; heavy bearing load, similar to the Fuji 'NAGAFU 12'.
- *Hardiness.*—Similar to standard Fuji.
- *Average size at maturity.*—Height: About 7 to 9 feet. Spread: About 5 to 7 feet. Caliper (at 12 inches above ground): About 3 to 5 inches.
- *Density.*—About 3,000 trees per hectare.
- *Production.*—About 18–20 Kg kg per tree.
- *Trunk.*—Texture: Smooth, with prominent lenticels. Color: Brownish grey, MBC #2.5Y 6/2.
- *Trunk lenticels.*—Length: About 2.02 mm. Width: About 0.85 mm. Color: Grey-brown, MBC #2.5Y 9/2. Density: About 3.5 n°/cm$^2$.

Branches:
- *Number per tree.*—About 16–18.
- *Angle.*—At emergence, angles range from 45 to 90 degrees.
- *Length.*—Varies due to pyramidal shape of tree. At 3 years, maximum about 80 cm to 90 cm; minimum about 20 cm.
- *Diameter.*—About 9 mm to 15 mm at 3 years old.
- *Texture.*—Pubescence on new wood, becoming glabrous on older wood.
- *Color.*—New wood: MBC #2.5Y 8.5/2; One year dormant shoot: MBC #5/YR 3/4; Two-year branch: MBC #10YR 5/2.
- *Internodes.*—Length (on one-year old shoots): About 28.7 mm. Diameter (on one-year old shoots): About 5.2 mm.
- *Branch lenticels.*—Length: About 1.53 mm. Width: About 0.54 mm. Shape: Elongated. Color: Tan, MBC #2.5Y 8.5/2. Density: About 8 to 10 n°/cm$^2$.

Leaves:
- *Arrangement.*—Alternate.
- *Size* (*average of 10 leaves in June, 2006 in S. Giuseppe di Comacchio (Ferrara), Italy).— Length: Range from* 60 to 100 mm; average 78 mm. Width: Range from 40 to 60 mm; average 51 mm.
- *Overall shape.*—Elliptical elongated.
- *Base shape.*—Obtuse.
- *Apex shape.*—Sharply pointed.
- *Margin.*—Finely serrate.
- *Texture.*—Upper surface Glossy, with fine pubescence along veins. Lower surface: Finely pubescent and covering entire surface.
- *Attitude in relation to shoot.*—Outwards.
- *Color.*—Mature leaves, upper surface: MBC #5GY 4/8. Mature leaves, lower surface: MBC #5GY 6/4. Immature leaves, upper surface: MBC #5GY 5/8. Immature leaves, lower surface: MBC #5GY 7/4.
- *Venation.*—Type: Pinnate. Color: MBC #5GY 8/4.
- *Petiole.*—Length: About 20 to 30 mm. Diameter: About 1.7 to 1.9 mm. Texture: Finely pubescent. Color: MBC #5GY 8/4.
- *Stipules.*—Arrangement: In pairs, thin, pointed. Length: About 10 mm. Width: About 1.1 mm.
- *Spur.*—Present. Distance between each spur: On the three year old branches, the distance is about 25 mm to 55 mm. Number of fruit per spur: 2 to 4.

Inflorescence:
- *Blooming period* (*in S. Giuseppe di Comacchio Ferrara, Italy*).—First bloom: Midseason, Apr. 17, 2006; Full bloom: Apr. 23, 2006.
- *Bloom duration.*—About 16 days. Varies with growing conditions.
- *Fragrance.*—Light, no apparent difference from other apple blossoms.
- *Number of flowers per inflorescence.*—About (please provide number).
- *Appearance.*—Identical to those of Fuji 'NAGAFU 12'.
- *Size.*—Medium to large, about 35–45 mm in diameter.

*Buds.*—Arrangement: Alternate. Length: About 7 mm. Width: About 4 mm. Color: Red, MBC #2.5R 7/6.

*Petals.*—Number per flower: 5. Length: About 20.8 mm. Width: About 13.8 mm. Overall shape: Ellipsoid. Apex shape: Between obtuse and slightly acute. Base shape: Obtuse. Texture: Smooth. Margin: Slightly crenate. Color (opened): Upper surface: White, Lower surface: White, with slight tingle of pink, MBC #2.5R 7/6. Color (unopened): Purplish-pink, MBC #2.5R 6/16.

*Sepals.*—Number per flower: About 5. Length: About 8.3 mm. Width: About 3.5 mm. Overall shape: Wedge-shaped, recurved downward. Apex shape: Acute. Texture: Pubescent (both surfaces). Margin: Entire. Color: MBC #2.5GY 7/7.

Reproductive organs:

*Androecium.*—Stamen: Number per flower: About 18, single row. Length: About 9.5 mm. Filament: Length: About 8 mm. Color: White green, MBC #5GY 9.5/1. Anther: Length: About 2.13 mm, diameter about 1.5 mm. Color: Bright yellow, MBC #2.5Y 8.5/12. Pollen: Amount: Medium. Color: Bright yellow, MBC #2.5Y 8.5/12. Pollination requirements: Believed compatible with all cultivars except Fuji, which bloom in the same time period.

*Gynoecium.*—Pistils: Number per flower: 1. Shape: Flat at top, rounded at base. Length: About 12.5 mm. Stigma: Length: Medium, about 0.3 mm. Color: Yellow-green, MBC #2.5GY 9/8. Style: Number: 5 styles, fused at base. Color: MBC #2.5GY 8/8.

Fruit:

*Keeping quality.*—Excellent; quality is similar to that of standard Fuji. Fruit remains crisp at room temperature for 2 weeks or more. Quality can be maintained up to 9 months in common storage at 0° C., and up to 12 months in controlled atmosphere (CA) storage.

*Maturity when described.*—Late harvest period (early October).

*Maturity period after full bloom.*—About 5.8 months after full bloom.

*Date of picking.*—Late harvest period (early October).

*Shape and appearance.*—Round to slight flat; usually symmetric; length/diameter ratio about 1:1, ribbing absent, lacking lobes at calyx end.

*Size.*—Medium to large; box 72 (about 83.6 mm); box 100 (about 74.4 mm).

*Weight.*—About 230 g.

*Stem.*—Length: Medium, about 26 mm. Width: Medium, about 2.2 mm. Color: Green, MBC #5GY 7/10 and greyed-red on the surface exposed to sunlight, MBC #5R 4/10.

*Basin.*—Depth: Medium, about 10 mm. Width: From 30 to 35 mm. Texture: Lightly pubescent at base.

*Calyx.*—Depth: Medium, about 9.25 mm. Width: Broad, about 34.7 mm.

*Crowning at calyx end.*—About or very weak.

*Calyx tube.*—Short and closed.

*Skin.*—Appearance: Thin, tender, glossy, very slow to become oily in storage, not prone to russet, slight tendency to cracking around cavity as fruit becomes over-mature. Thickness: About 0.3 mm. Texture: Glossy. General Color Effect: Prominently blushed, more colored than any red Fuji strain yet observed, including 'NAGAFU 12', 'NAGAFU 6', 'RAKU RAKU', and 'T.A.C. #114'. Overcolor of the skin: Prominently blushed, MBC #8.5R 6/16 with some stripes, MBC #5R 4/12. Percentage of skin surface with overcolor: About 80%. Pattern of overcolor: Striped. Background color of the skin: MBC #5Y 8/10 at optimum maturity, from MBC #10 Y 8/10 at early picking maturity. Russet: Generally absent, but similar to standard Fuji, which can show occasional russet caused by environment or caustic sprays.

*Lenticels.*—Size: Small. Appearance: Inconspicuous. Shape: Round. Length: About 0.5 mm. Width: About 0.5 mm. Color: MBC #7.5Y 8.5/6. Density: About 4 $n^o/cm^2$.

*Flesh.*—Color: Cream, MBC #5Y 8.5/4. Texture: Crisp and juicy. Aroma: Moderate. Eating quality: Juicy, sweet, non-astringent. Firmness (at harvest): About 17 to 20 pounds. Soluble solids: About 14 to 16%. Sugar Content: 12 to 15 Brix. Starch Index (1–6 scale): About 3 to 3.5. Acid content: 0.5% malic acid.

*Core.*—Symmetry of core: Bundle area round, 10 bundles. Distinctness of core lines: Weakly defined. Width: About 27 mm. Length: About 23 mm.

*Locules.*—Number (per fruit): 5, tight, closed. Size: Medium to small. Shape: Partly open. Length: About 11 mm. Width: About 4.5 mm.

*Seeds.*—Number: About 2 per cell, tightly adhering to the carpel wall. Shape: Obovate. Length: About 8 mm. Width: About 5 mm. Color: Reddish-brown, MBC #7.5YR 3/6.

Use: Fresh market, dessert apple.

Disease and insect resistance: Similar to standard Fuji; no unusual resistance or susceptibility observed as of this time.

Resistance to pests and diseases: For both the tree and fruit, identical to standard Fuji apple trees and other commonly used Fuji varieties known to the inventor.

Winter hardiness: Tolerant to temperatures down to about −10° C. without observed damage to wood and buds of dormant apple trees.

Drought/heat tolerance: Tolerant to temperatures up to about 35° C., growth is limited by drought periods without irrigation.

We claim:

1. A new and distinct *Malus domestica* apple tree plant named 'FUJIKO', as illustrated and described herein.

* * * * *